US011915792B2

(12) United States Patent
Walia et al.

(10) Patent No.: US 11,915,792 B2
(45) Date of Patent: Feb. 27, 2024

(54) METHOD AND A SYSTEM FOR PROFILING OF METAGENOME

(71) Applicant: Tata Consultancy Services Limited, Mumbai (IN)

(72) Inventors: Vidushi Walia, Hyderabad (IN); Naveen Sivadasan, Hyderabad (IN); Rajgopal Srinivasan, Hyderabad (IN); Kota Krishna Priya, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 120 days.

(21) Appl. No.: 17/737,106

(22) Filed: May 5, 2022

(65) Prior Publication Data

US 2022/0392565 A1 Dec. 8, 2022

(30) Foreign Application Priority Data

May 6, 2021 (IN) .............................. 202121020744

(51) Int. Cl.
*G16B 10/00* (2019.01)
*G06F 16/22* (2019.01)
*G16B 30/10* (2019.01)
*G16B 40/20* (2019.01)

(52) U.S. Cl.
CPC ......... *G16B 10/00* (2019.02); *G06F 16/2228* (2019.01); *G16B 30/10* (2019.02); *G16B 40/20* (2019.02)

(58) Field of Classification Search
CPC ........ G16B 10/00; G16B 30/10; G16B 40/20; G06F 16/2228
See application file for complete search history.

(56) References Cited

U.S. PATENT DOCUMENTS

| 2018/0293485 A1* | 10/2018 | Merhav | G06N 3/04 |
| 2018/0363012 A1* | 12/2018 | Burk | C12P 7/40 |
| 2019/0318807 A1* | 10/2019 | O'Hara | G16B 50/10 |

(Continued)

OTHER PUBLICATIONS

Bouchot et al: "Advances in Machine Learning for Processing and Comparison of Metagenomic Data", 2013, Drexel University, 3141 Chestnut street, 19104 (Year: 2013).*

(Continued)

*Primary Examiner* — Kuen S Lu
(74) *Attorney, Agent, or Firm* — FINNEGAN, HENDERSON, FARABOW, GARRETT & DUNNER, LLP

(57) ABSTRACT

This disclosure relates generally to a method and a system for profiling of metagenome samples. Most state of-art techniques for metagenomic profiling use homology-based, curated database of identified marker sequences generated after complex and costly pre-processing. The disclosed method and system for profiling of metagenome samples are a non-homology based, a non-marker based and an alignment free strain level profiling tools for microbe profiling. The disclosure works with a several k-mer based indexing techniques for constructing a compact and comprehensive multi-level indexing, wherein the multi-level indexing includes a L1-Index and a L2-Index. The multi-level indexing is used for profiling metagenomics by abundance estimation, wherein the abundance estimation includes a relative abundance and an absolute abundance.

15 Claims, 6 Drawing Sheets

(56) References Cited

U.S. PATENT DOCUMENTS

| | | | |
|---|---|---|---|
| 2020/0192889 A1* | 6/2020 | Chang | G16H 50/20 |
| 2021/0079447 A1* | 3/2021 | Ismagilov | C12Q 1/686 |
| 2023/0257317 A1* | 8/2023 | Temme | C12N 15/52 |
| | | | 71/7 |

OTHER PUBLICATIONS

Koslicki et al., "MetaPalette: a κ-mer Painting Approach for Metagenomic Taxonomic Profiling and Quantification of Novel Strain Variation," mSystems, 1(3):e00020-16 (2016).

Mahe et al., "Predicting bacterial resistance from whole-genome sequences using κ-mers and stability selection," BMC Bioinformatics, 19:383 (2018).

Qian et al., "MetaCon: unsupervised clustering of metagenomic contigs with probabilistic k-mers statistics and coverage," BMC Bioinformatics, 20(Suppl 9):367 (2019).

Tu et al., "HuMiChip2 for strain level identification and functional profiling of human microbiomes," Appl Microbiol Biotechnol, 101 (2017).

\* cited by examiner

METHOD AND A SYSTEM FOR PROFILING OF METAGENOME

PRIORITY CLAIM

This U.S. patent application claims priority under 35 U.S.C. § 119 to: India Application No. 202121020744, filed on May 6, 2021. The entire contents of the aforementioned application are incorporated herein by reference.

TECHNICAL FIELD

The disclosure herein generally relates to the field of identifying microbial population, and, more particularly, to a method and a system for profiling of metagenome samples, where profiling includes identification and quantification of metagenomic samples at different levels of taxonomy hierarchy including at a strain level.

BACKGROUND

Metagenomics research enables detailed characterization of environmental or host-associated microbial communities. The metagenomics research has several applications including clinical study, disease study, study of environmental habitats, characterizing an industrial product and study of host-pathogen interactions. One of the powerful ways of examining the diversity and complexity of microbial communities in metagenomics research/metagenomic analysis is metagenomic sequencing.

An essential prerequisite for any metagenomic analysis is to disentangle the microbial sample at lower ranks of taxonomy such as species/strain with precise measurements of their abundances. As the metagenomic samples are usually diverse and contain strains that share high genomic similarity. The high similarity in the genomic sequence of metagenomic samples makes estimation of taxonomic composition tremendously challenging, especially at the higher resolutions of species and strains.

Most state of-art techniques for metagenomic analysis use curated database of identified marker sequences generated after complex and costly pre-processing, including phylogeny analysis, of reference sequences. However, use of specific marker sequences often has difficulty in accurate strain level profiling due to limited read support. Furthermore, incorporating new sequences or modifying the reference data can be very expensive.

Another popular technique for metagenomic sample analysis is homology based microbial profiling approach. The homology based microbial profiling approaches that are dependent on the similarity of microbial sequences requires complex computation, intensive pre-processing the reference database in order index the reference genome collection. However, the homology approaches work only on selected subset of markers, thus eliminating major portion of the database, which leads to estimation errors due to reduced read support while estimating the abundances. Furthermore, for such techniques, significant amount of re-indexing and pre-processing is often required to incorporate updates to the reference genome collection. Thus, there is a requirement for a non-homology based and alignment free profiling tool that can disentangle the metagenomic samples down to the level of Species/Strain.

SUMMARY

Embodiments of the present disclosure present technological improvements as solutions to one or more of the above-mentioned technical problems recognized by the inventors in conventional systems. For example, in one embodiment, a method for profiling of metagenome sample is provided.

The system is configured for receiving a plurality of reference microbial sequences, via one or more hardware processors, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier. The system is further configured to segregating the plurality of reference microbial sequences to obtain a plurality of pre-defined reference chunks using a segregation technique based on the plurality of genus, via the one or more hardware processors, wherein the plurality of pre-defined reference chunks comprises the plurality of strain level sequences belonging to the plurality of genus and the plurality of pre-defined reference chunks is associated with a plurality of indices. The system is further configured for indexing the plurality of pre-defined reference chunks to generate a L1-Index and L2-Index based on an L1-L2 indexing technique, via the one or more hardware processors, wherein the L1-L2 indexing technique comprises: generating a L2-Index from the plurality of pre-defined reference chunks, wherein generation of the L2-Index comprises: generating a plurality of L2 k-mers from the plurality of strain level sequences of the plurality of pre-defined reference chunks using on a k-merization technique based on a pre-defined L2 k-value; indexing each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier; generating a L1-Index from the plurality of pre-defined reference chunks, wherein generation of the L1-Index comprises: generating a plurality of L1 k-mers from the plurality of strain level sequences of the plurality of pre-defined reference chunks using on the k-merization technique based on a pre-defined L1 k-value; indexing the plurality of L1 k-mers to obtain the L1-Index based on a binary encoding technique and a numerical encoding technique, wherein the L1-Index is a map of the L1 k-mers and the indices of the plurality of pre-defined reference chunks. The system is further configured for receiving a plurality of microbial read sequences, via one or more hardware processors, wherein the microbial read sequences is a metagenome sample and each microbial read sequence from the plurality of microbial read sequences is associated with a read length and a sequencing depth. The system is further configured for profiling the plurality of microbial read sequences, via one or more hardware processors, based on the L1-Index and the L2-Index, wherein the profiling the plurality of microbial read sequences at a profile taxonomic hierarchy comprises: generating a plurality of L1 query k-mers and a plurality of L2 query k-mers for the plurality of microbial read sequences based on a pre-defined L1 k-value and a pre-defined L2 k-value respectively using the k-merization technique; identifying from the L1-index, a matching reference plurality of pre-defined reference chunks and the corresponding plurality of indices for the plurality of L1 query k-mers; identifying from the L2-Index, the plurality of strain level sequences and the internal unique reference identifier for the plurality of L2 query k-mers based on the matching reference plurality of pre-defined reference chunks and the plurality of indices; profiling the plurality of microbial read sequences, wherein the profiling comprises performing an abundance estimation of the plurality of strain level sequences based on an estimation technique using the strain level sequences, the internal unique reference identifier and the sequence length.

In another aspect, a method for profiling of metagenome sample is provided. The method includes receiving a plurality of reference microbial sequences, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier. The method includes segregating the plurality of reference microbial sequences to obtain a plurality of pre-defined reference chunks using a segregation technique based on the plurality of genus, wherein the plurality of pre-defined reference chunks comprises the plurality of strain level sequences belonging to the plurality of genus and the plurality of pre-defined reference chunks is associated with a plurality of indices. The method includes indexing the plurality of pre-defined reference chunks to generate a L1-Index and L2-Index based on an L1-L2 indexing technique, wherein the L1-L2 indexing technique comprises: generating a L2-Index from the plurality of pre-defined reference chunks, wherein generation of the L2-Index comprises: generating a plurality of L2 k-mers from the plurality of strain level sequences of the plurality of pre-defined reference chunks using on a k-merization technique based on a pre-defined L2 k-value; indexing each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier; generating a L1-Index from the plurality of pre-defined reference chunks, wherein generation of the L1-Index comprises: generating a plurality of L1 k-mers from the plurality of strain level sequences of the plurality of pre-defined reference chunks using on the k-merization technique based on a pre-defined L1 k-value; indexing the plurality of L1 k-mers to obtain the L1-Index based on a binary encoding technique and a numerical encoding technique, wherein the L1-Index is a map of the L1 k-mers and the indices of the plurality of pre-defined reference chunks. The method includes receiving a plurality of microbial read sequences, wherein the microbial read sequences is a metagenome sample and each microbial read sequence from the plurality of microbial read sequences is associated with a read length and a sequencing depth. The method includes profiling the plurality of microbial read sequences, based on the L1-Index and the L2-Index, wherein the profiling the plurality of microbial read sequences at a profile taxonomic hierarchy comprises: generating a plurality of L1 query k-mers and a plurality of L2 query k-mers for the plurality of microbial read sequences based on a pre-defined L1 k-value and a pre-defined L2 k-value respectively using the k-merization technique; identifying from the L1-index, a matching reference plurality of pre-defined reference chunks and the corresponding plurality of indices for the plurality of L1 query k-mers; identifying from the L2-Index, the plurality of strain level sequences and the internal unique reference identifier for the plurality of L2 query k-mers based on the matching reference plurality of pre-defined reference chunks and the plurality of indices; profiling the plurality of microbial read sequences, wherein the profiling comprises performing an abundance estimation of the plurality of strain level sequences based on an estimation technique using the strain level sequences, the internal unique reference identifier and the sequence length.

In yet another aspect, a non-transitory computer readable medium for profiling of metagenome sample is provided. The program includes receiving a plurality of reference microbial sequences, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier. The program includes segregating the plurality of reference microbial sequences to obtain a plurality of pre-defined reference chunks using a segregation technique based on the plurality of genus, wherein the plurality of pre-defined reference chunks comprises the plurality of strain level sequences belonging to the plurality of genus and the plurality of pre-defined reference chunks is associated with a plurality of indices. The program includes indexing the plurality of pre-defined reference chunks to generate a L1-Index and L2-Index based on an L1-L2 indexing technique, wherein the L1-L2 indexing technique comprises: generating a L2-Index from the plurality of pre-defined reference chunks, wherein generation of the L2-Index comprises: generating a plurality of L2 k-mers from the plurality of strain level sequences of the plurality of pre-defined reference chunks using on a k-merization technique based on a pre-defined L2 k-value; indexing each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier; generating a L1-Index from the plurality of pre-defined reference chunks, wherein generation of the L1-Index comprises: generating a plurality of L1 k-mers from the plurality of strain level sequences of the plurality of pre-defined reference chunks using on the k-merization technique based on a pre-defined L1 k-value; indexing the plurality of L1 k-mers to obtain the L1-Index based on a binary encoding technique and a numerical encoding technique, wherein the L1-Index is a map of the L1 k-mers and the indices of the plurality of pre-defined reference chunks. The program includes receiving a plurality of microbial read sequences, wherein the microbial read sequences is a metagenome sample and each microbial read sequence from the plurality of microbial read sequences is associated with a read length and a sequencing depth. The program includes profiling the plurality of microbial read sequences, based on the L1-Index and the L2-Index, wherein the profiling the plurality of microbial read sequences at a profile taxonomic hierarchy comprises: generating a plurality of L1 query k-mers and a plurality of L2 query k-mers for the plurality of microbial read sequences based on a pre-defined L1 k-value and a pre-defined L2 k-value respectively using the k-merization technique; identifying from the L1-index, a matching reference plurality of pre-defined reference chunks and the corresponding plurality of indices for the plurality of L1 query k-mers; identifying from the L2-Index, the plurality of strain level sequences and the internal unique reference identifier for the plurality of L2 query k-mers based on the matching reference plurality of pre-defined reference chunks and the plurality of indices; profiling the plurality of microbial read sequences, wherein the profiling comprises performing an abundance estimation of the plurality of strain level sequences based on an estimation technique using the strain level sequences, the internal unique reference identifier and the sequence length.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
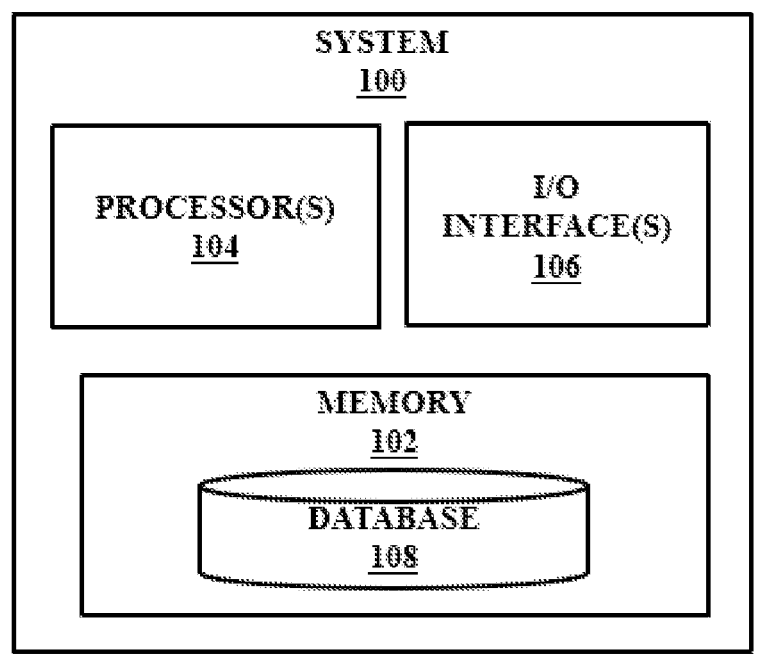
FIG. 1 illustrates an exemplary system for profiling of metagenome sample according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Glossary

Microbiome Profiling is the identification of the microbial communities, in vivo or in vitro. The metagenomic profiling from sequencing data aims to disentangle a microbial sample at lower ranks of the taxonomy such as species and strains with precise measurement of abundances.

Homology based techniques are for microbial analysis wherein homology refers to similarity of the structure, sequence, physiology, or development of different species of organisms based upon their descent from a common evolutionary ancestor.

Query k-mer refers to a substring of length 'k' generated from a read sequence in a metagenomic sample.

Read Mapping refers to assignment of the read sequence from a metagenomic sample to specific matching regions in the reference sequence.

Microbial Abundance Estimation comprises all statistical methods for estimating the quantity of microbes in a metagenomic sample.

Referring now to the drawings, and more particularly to FIG. 1 through FIG. 3D, where similar reference characters denote corresponding features consistently throughout the figures, there are shown preferred embodiments and these embodiments are described in the context of the following exemplary system and/or method.

FIG. 1 is an exemplary block diagram of a system 100 for profiling of metagenome sample in accordance with some embodiments of the present disclosure. The profiling of metagenome sample includes identification and quantification of metagenomic samples at different levels of taxonomy hierarchy including at a strain level. The taxonomic hierarchy comprises one or more of a plurality of phyla, a plurality of classes, a plurality of orders, a plurality of families, a plurality of genera, a plurality of species, a plurality of subspecies and a plurality of strains.

In an embodiment, the system 100 includes a processor(s) 104, communication interface device(s), alternatively referred as input/output (I/O) interface(s) 106, and one or more data storage devices or a memory 102 operatively coupled to the processor(s) 104. The system 100 with one or more hardware processors is configured to execute functions of one or more functional blocks of the system 100.

Referring to the components of the system 100, in an embodiment, the processor(s) 104, can be one or more hardware processors 104. In an embodiment, the one or more hardware processors 104 can be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 is configured to fetch and execute computer-readable instructions stored in the memory 102. In an embodiment, the system 100 can be implemented in a variety of computing systems including laptop computers, notebooks, hand-held devices such as mobile phones, workstations, mainframe computers, servers, a network cloud and the like.

The I/O interface(s) 106 can include a variety of software and hardware interfaces, for example, a web interface, a graphical user interface, a touch user interface (TUI) and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 106 can include one or more ports for connecting a number of devices (nodes) of the system 100 to one another or to another server.

The memory 102 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

Further, the memory 102 may include a database 108 configured to include information regarding extraction of tasks, labelling of words, performing pre-processing of received documents. The memory 102 may comprise information pertaining to input(s)/output(s) of each step performed by the processor(s) 104 of the system 100 and methods of the present disclosure. In an embodiment, the database 108 may be external (not shown) to the system 100 and coupled to the system via the I/O interface 106.

Figure 2:
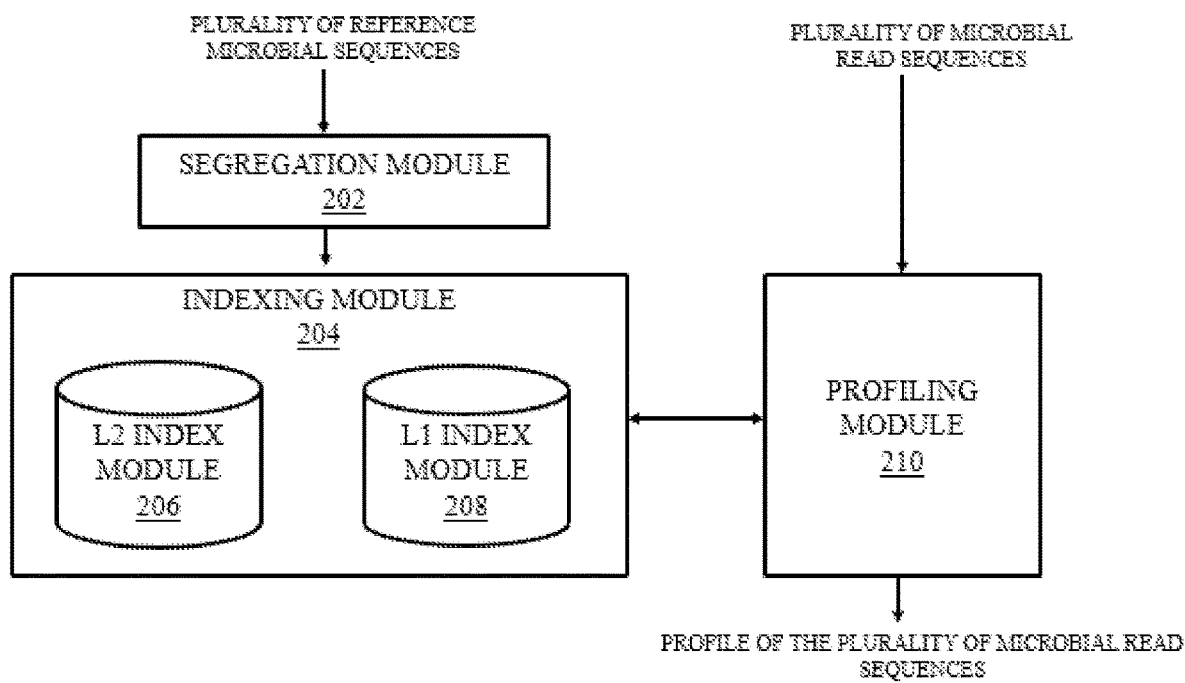
FIG. 2 is a functional block diagram according to some embodiments of the present disclosure.
Figure 3A:
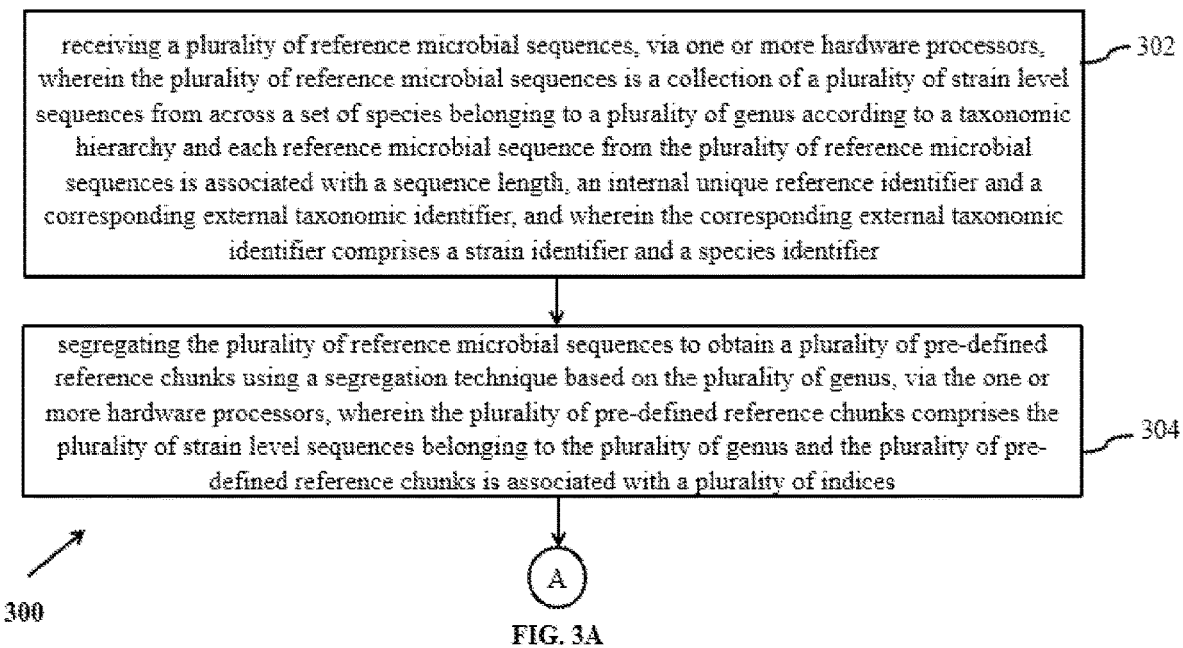
FIG. 3A through FIG. 3D is a flow diagram illustrating profiling of metagenome sample in accordance with some embodiments of the present disclosure.
Figure 3B:
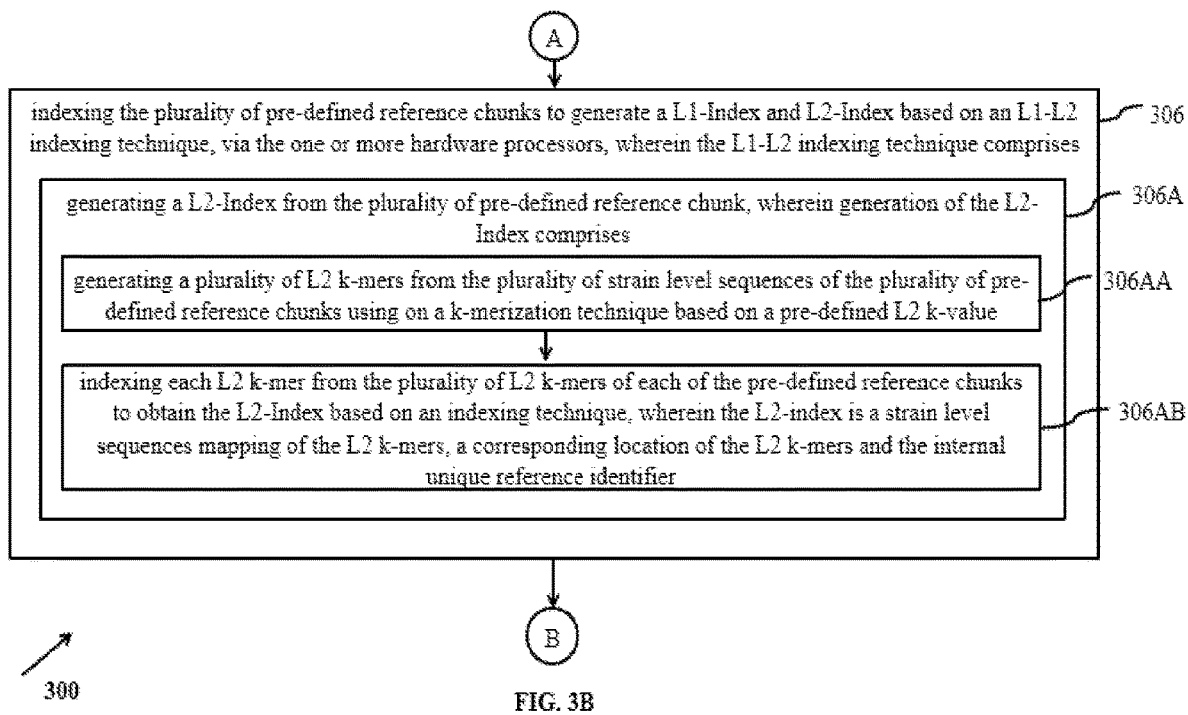
Figure 3C:
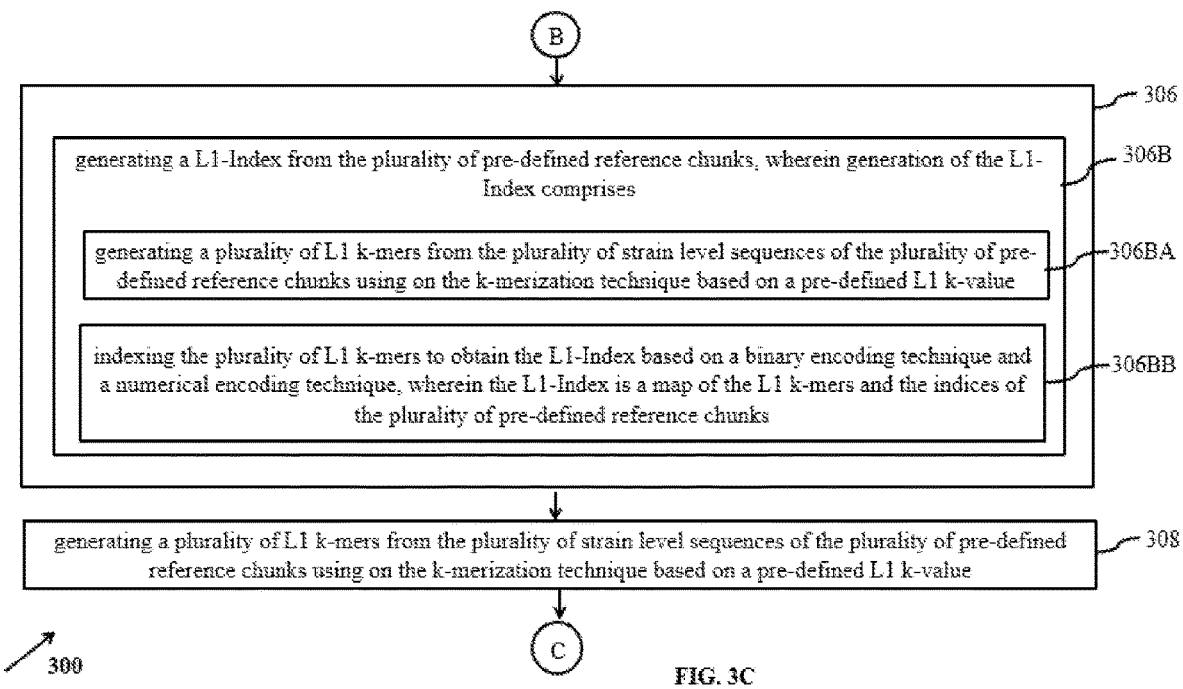
Figure 3D:
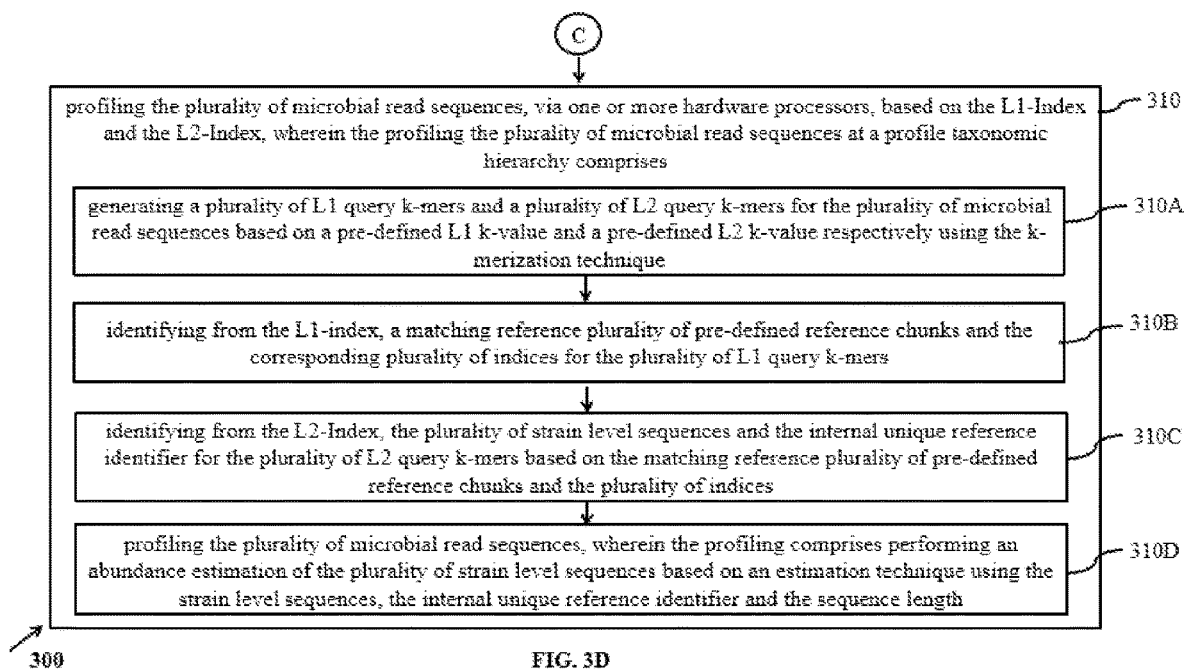

Functions of the components of system 100 are explained in conjunction with functional overview of the system 100 in FIG. 2 and flow diagram of FIG. 3 for extraction of tasks from documents using weak supervision.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

FIG. 2 is an example functional block diagram of the various modules of the system of FIG. 1, in accordance with some embodiments of the present disclosure. As depicted in the architecture, the FIG. 2 illustrates the functions of the modules of the system 100 that includes profiling of metagenome sample. The method and system for profiling of metagenome sample are a non-homology based and alignment free profiling tools that can disentangle the metagenomic samples down to the level of Species/Strain. The disclosed techniques work with a k-mer based index of the reference data.

The system 200 further comprises a segregation module 202 configured for segregating the plurality of reference microbial sequences to obtain a plurality of pre-defined reference chunks using a segregation technique. The system 200 further comprises an indexing module 204 configured for indexing the plurality of pre-defined reference chunks to generate a L1-Index at a L1 index module 208 and L2-Index at a L2 index module 206. The system 200 further comprises a profiling module 210 configured for profiling the plurality of microbial read sequences based on the L1-Index and the L2-Index.

The various modules of the system 100 and the functional blocks in FIG. 2 are configured for profiling of metagenome sample are implemented as at least one of a logically self-contained part of a software program, a self-contained hardware component, and/or, a self-contained hardware component with a logically self-contained part of a software program embedded into each of the hardware component that when executed perform the above method described herein.

Functions of the components of the system 200 are explained in conjunction with functional modules of the system 100 stored in the memory 102 and further explained in conjunction with flow diagram of FIGS. 3A-3D. The FIGS. 3A-3D with reference to FIG. 1, is an exemplary flow diagram illustrating a method 300 for profiling of metagenome sample using the system 100 of FIG. 1 according to an embodiment of the present disclosure.

The steps of the method of the present disclosure will now be explained with reference to the components of the system (100) for profiling of metagenome sample and the modules (202-210) as depicted in FIG. 2 and the flow diagrams as depicted in FIGS. 3A-3D. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At step 302 of the method (300) a plurality of reference microbial sequences is received, via one or more hardware processors 104.

The plurality of reference microbial sequences is a collection of a plurality of strain level sequences from across a set of species belonging to a plurality of genus according to a taxonomic hierarchy. The taxonomic hierarchy comprises one or more of a plurality of phyla, a plurality of classes, a plurality of orders, a plurality of families, a plurality of genera, a plurality of species, a plurality of subspecies and a plurality of strains.

Each reference microbial sequence from the plurality of reference microbial sequences is associated with:
(a) a sequence length,
(b) an internal unique reference identifier, and;
(c) a corresponding external taxonomic identifier for the internal unique reference identifier, The external taxonomic identifier comprises a strain identifier and a species identifier, wherein the entire microbial hierarchy or the taxonomic hierarchy can be retrieved using the external taxonomic identifier.

In an example scenario, the plurality of reference microbial sequences is represented as S;

$$S=\{s_1, \ldots s_N\}$$

Where N: is the collection of N input sequences.

For each reference microbial sequence (S), there is an associated internal unique reference identifier and S is sequences are a string of characters. The mapping between the internal identifiers and their corresponding external taxonomic identifier (strain identifier and species identifier) is maintained separately.

The plurality of reference microbial sequences is obtained from plurality of publicly available sources for biomedical data, which include National Center for Biotechnology Information (NCBI), Ensemble, UCSC Genome browser etc., In an example scenario, the plurality of reference microbial sequences is collected from Refseq, Mosaic Challenge and consisted of 24,146 strains from 13,168 species, wherein the species were from 3,559 genus belonging to Virus, Bacteria, Archae, Fungi and Protozoa with an index size of â˜¼ 38 GB. In an example scenario—The plurality of reference microbial sequences is string of characters comprising of a string of characters including "ATGCN".

At step 304 of the method (300), the plurality of reference microbial sequences is segregated to obtain a plurality of pre-defined reference chunks using a segregation technique based on the plurality of genus, via the segregation module 202. The plurality of pre-defined reference chunks comprises the plurality of strain level sequences belonging to the plurality of genus and the plurality of pre-defined reference chunks is associated with a plurality of indices.

In the present disclosure, the segregation technique includes segregating the plurality of reference microbial sequences into the plurality of pre-defined reference chunks (n). In an example scenario—the plurality of pre-defined reference chunks (n) can be of 32 chunks (clustered at Genus level) which are segregated using the segregation technique that includes a genus-level taxonomic classifier. The pre-defined reference chunks of 32 chunks are further indexed using the FM Index (Full text index in Minute space) libraries and the R Index achieves further compression by exploiting the repetitive patterns in the reference sequences. The FM Index is a compressed space economical substring index structure which is based on Burrows Wheeler Transform (BWT). The FM Index is used to search arbitrary patterns in the given text/string and allows compression of the input without compromising the speed of querying. Further, the partitioning is balanced in the sense that all pre-defined reference chunks have comparable sizes, and each sub-collection has no more than 4 GB of total genomic data. Thus, allowing using efficient 32-bit implementations of the FM index and the R Index. In an example scenario—a whole collection of around 24000 (24k) genomic sequences is partitioned into 32 pre-defined reference chunks for L1 index and L2 index. All strains from a species are part of the same sub-collection and a sub-collection can contain one or more species.

The plurality of reference microbial sequences (S) is segregated into plurality of pre-defined reference chunks (S), $$S=S_1 \cup \ldots S_T,$$

wherein:
T is total number of non-overlapping sub-collections, and each sub-collection $S_i$ is a subset S.

At step 306 of the method (300), the plurality of pre-defined reference chunks is indexed, via the indexing module 204. The plurality of pre-defined reference chunks is indexed to generate a L1-Index and L2-Index based on an L1-L2 indexing technique. The L1-L2 indexing technique comprises:
  (a) generating a L2-Index from the plurality of pre-defined reference chunks at the L2 index module 206, and
  (b) generating a L1-Index from the plurality of pre-defined reference chunks at the L1 index module 208.

The indexing technique comprises one of a FM Indexing technique, a R Indexing technique, a bowtie indexing technique, a suffix tree or suffix array technique, a Rabin-Karp technique, a KMP (Knuth Morris Pratt) technique, a Boyer Moore technique and a De Bruijn Graph.

The step 306A of the method 300 explains the process of generating the L2-Index from the plurality of pre-defined reference chunks comprising the following steps:

At step 306AA of the method (300), a plurality of L2 k-mers is generated from the plurality of strain level sequences of the plurality of pre-defined reference chunks using on a k-merization technique based on a pre-defined L2 k-value. The pre-defined L2 k-value is represented as a "k".

In an embodiment, the k-merization technique includes generation of a plurality of k-mers from the plurality of pre-defined reference chunks, wherein the plurality of pre-defined reference chunks is in form of a string of characters and the generated k-mers are sub-strings of a pre-defined length 'k' from the string of characters. The k-merization technique generates constituent k-mers of length 'k' from plurality of strain level sequences (or any microbial sequence). The constituent kmers are substring of length 'k' that are generated by sliding a window of length 'k' over the plurality of strain level sequences. The resultant k-mers are such that each consecutive k-mer overlap by k−1 characters. For plurality of strain level sequences (or any microbial sequence) of length 'l' and k-mer of length 'k', a total of l−k+1 kmers can be generated.

In an embodiment, the pre-defined L2 k-value (k) is dynamically determined based on (a) a smaller value of k will ensure that the true sequences receive sufficient k-mer hits even under sequencing errors. However, this can also increase the hits for false positives, or (b) a larger value of k on the other hand will reduce the total false positive hits while at the same time impacting the total true positive hits due to the presence of sequencing errors.

At step 306AB of the method (300), each L2 k-mer from the plurality of L2 k-mers of each of the pre-defined reference chunks is indexed to obtain the L2-Index based on an indexing technique, wherein the L2-index is a strain level sequences mapping of the L2 k-mers, a corresponding location of the L2 k-mers and the internal unique reference identifier. The L2-index search/query function is represented as $m_k(x, t)$, where x represents a query kmer and t is the represents the pre-defined reference indices.

The indexing technique includes one of the FM Index (Full text index in Minute space) and the R Index.

Considering an example scenario where the L2 Index is obtained by the T pre-defined reference chunks of the plurality of pre-defined reference chunks by indexing each pre-defined reference chunks separately using the FM index based full text indexing that supports k-mer lookup. In particular, standard FM index or R index is utilized to index each of the T pre-defined reference chunks. Of the 32 pre-defined reference chunks (of the plurality of pre-defined reference chunks), 23 pre-defined reference chunks were of single species. Such pre-defined reference chunks are ideally indexed using R Index due to the large number of highly similar strains falling under the same species. The remaining 9 pre-defined reference chunks are indexed using FM Index. The sequences in a sub-collection are concatenated while indexing. The hit locations obtained while querying a k-mer in a sub-collection index is mapped to the matching sequence IDs by efficiently searching against the sequence start locations in the concatenated sequence. The resulting level 2 search $m_k{}'(x, t)$ efficiently returns the set of all sequence identities from the sub-collection $S_t$ that contain the query k-mer x.

The step 306B of the method 300 explains the process of generating the L1-Index from the plurality of pre-defined reference chunks comprising the following steps:

At step 306BA of the method (300), a plurality of L1 k-mers is generated from the plurality of strain level sequences of the plurality of pre-defined reference chunks using on the k-merization technique based on a pre-defined L1 k-value, wherein the pre-defined L1 k-value is represented as 'k"

In an embodiment, the pre-defined L1 k-value 'k' affects the total L1 index size. Here again, smaller 'k' increases the total false positive hits. Larger 'k' on the other hand reduces false positive hits and at the same time also affects the true positive hits due to the presence of sequencing errors.

At step 306BB of the method (300), the plurality of L1 k-mers is indexed to obtain the L1-Index based on a binary encoding technique and a numerical encoding technique, wherein the L1-Index is a map of the L1 k-mers and the indices of the plurality of pre-defined reference chunks.

In an embodiment, the level 1 index (L1 index) is a meta-index which maps a query k-mer x to a subset of $\{1, \ldots, T\}$ denoting the subset of the level 2 pre-defined reference chunks each having at least one occurrence of the query k-mer x. The k-mer length used in the L1 index (meta-index) can be different from the k-mer length used at the L2 index. The L1 index is constructed by creating a T length binary characteristic vector for each k-mer x that encodes its corresponding subset of $\{1, \ldots, T\}$. The characteristics vectors are ordered in the index based on the numerical encoding of the associated k-mer. The resulting L1 index search function $f_k{}'(x)$ efficiently returns the subset of $\{1, \ldots, T\}$ corresponding to the characteristic binary vector for the k–mer x.

At step 308 of the method (300), a plurality of microbial read sequences is received, via the hardware processors 104. The plurality of microbial read sequences is a metagenome sample and each microbial read sequence from the plurality of microbial read sequences is associated with a read length and a sequencing depth (c). The plurality of microbial read sequences is a string of characters.

In an embodiment, the plurality of microbial read sequences is received/collected from a variety of environment locations such as human body (gut, vaginal, stool, etc.), ocean, soil, and so on. The environment samples undergo high throughput sequencing to generate metagenomic read samples using high throughput sequencing platforms including a Illumina, a Pacbio, a Nanopore, etc. The plurality of microbial read sequences is a string of characters comprising of a string of characters including "ATGCN".

At step 310 of the method (300), the plurality of microbial read sequences is profiled, via the profiling module 210, based on the L1-Index and the L2-Index. The profiling is performed based on the profile taxonomic hierarchy, wherein the profile taxonomic hierarchy is dynamically selected from the taxonomic hierarchy by a user based on the user's requirement. In an example scenario, the user may require profiling at "strain level" of the taxonomic hierarchy or the user may require profiling at "phyla" level of the taxonomic hierarchy. Hence the use may decide dynamically to provide at one of the levels of the taxonomic hierarchy comprising: one or more of a plurality of phyla, a plurality of classes, a plurality of orders, a plurality of families, a plurality of genera, a plurality of species, a plurality of subspecies and a plurality of strains.

The process of profiling the plurality of microbial read sequences at a profile taxonomic hierarchy comprises:

At step 310A of the method (300), a plurality of L1 query k-mers and a plurality of L2 query k-mers is generated for the plurality of microbial read sequences based on the pre-defined L1 k-value (k') and the pre-defined L2 k-value (k) respectively using the k-merization technique.

In an embodiment, the two level search functions $f_{k'}(x)$ and $m_k(y, t)$ with pre-defined k-mer lengths k and k', read mapping for the plurality of microbial read sequences (r), wherein read mapping is like "querying phase" where 'n' read are generated from the metagenomic sample are assigned to specific reference sequence based on the matching sequence regions. For a read r, the L1 index is searched using $f_{k'}(x)$ for each k-mer x in the read r. Using the search outcomes, the top h' second level indices, for a predefined threshold h', are identified based on the cumulative k'—mer hits they received, wherein "hits" refers to the count of matching kmers after read mapping operation.

At step 310B of the method (300), a matching reference plurality of pre-defined reference chunks and the corresponding plurality of indices are identified for the plurality of L1 query k-mers from the L1-index.

From the plurality of selected indices every matching indexed predefined reference chunk $(S_j)$ from the plurality of indexed predefined reference chunks is then searched using $m_k(x, t)$ for each query k-mer y in the read. The final set of target sequences for the query read r, denoted by Q(r), is given by a subset of sequences from these selected indices, where each of these sequences received a cumulative k-mer hit greater than a pre-defined threshold h' The threshold parameters h and h' are chosen in such a way to reduce the overall search time while avoiding false hits.

At step 310C of the method (300), the plurality of strain level sequences and the corresponding internal unique reference identifier are identified from the L2-Index, for the plurality of L2 query k-mers. The plurality of strain level sequences and the internal unique reference identifier are identified based on the matching reference plurality of pre-defined reference chunks and the plurality of indices.

In an embodiment, for a read with average read length $\hat{r}$ and k-mer length k, the L2-Index pre-defined threshold parameter h can take any value in the range $\{1, \ldots \hat{r}-k+1\}$ lower value for threshold parameter h increases false positive hits while a larger value of h can lead to increased false negative hits. The L1-Indexpredefined threshold h' on the other hand governs the number of total numbers of indexed predefined reference chunks that should be selected for the L2 index search function. Larger value of h leads to increase in the overall search time while a lower value of h' leads to increased false negatives, such that the target second level index does not qualify for the L2 index read mapping.

At step 310D of the method (300), the plurality of microbial read sequences is profiled.

The profiling comprises performing an abundance estimation of the plurality of strain level sequences based on an estimation technique using the target level sequences, the internal unique reference identifier and the sequence length for each read sequence in the read collection.

The estimation technique is a mathematical estimation technique that includes one of a Maximum Likelihood Estimation technique, a Lasso regression technique, a Bayesian Estimation technique.

The abundance estimation includes a relative abundance and an absolute abundance. The absolute abundance is computed using the internal unique reference identifier, the external taxonomic identifier, the L2 index, the sequence length, the read length and the sequencing depth of the plurality of microbial read sequences.

In an embodiment, the relative strain level abundances are estimated using MLE (Maximum Likelihood Estimation), where for 'm' strains in S, R denotes the read set. Let the set of distinct strains present in the sample be $S^* \subseteq S$. Each read r in R is assumed to be generated randomly and independently from a source strain $s_i \in S^*$, where the source strain is sampled with probability $a_i$, which is the relative abundance of $s_i$ in the sample. It is simplifying assumed to be uniform coverage, which implies that the read is generated from a location in the source strain sampled uniformly at random, where the $x_i$ length adjusted relative abundance of strain i, such that $x_i$ is the relative fraction of the total size of strain i microbial sequences in the metagenomic sample;

$$Pr(R \mid x) = \prod_{r \in R} \sum_{s_j \in Q(r)} \frac{x_j}{l'_j}$$

Wherein,
Pr is the sampling probability of strain S (reflective of the relative abundance of the strain),
R is the plurality of microbial read sequences in sample,
r is a read in the plurality of microbial read sequences,
Q is the set of mapped read sequences as a result of L2 index search,
s is the distinct strains present in the Q(r),
j is the unique internal identifier, which is associated to an external taxonomic identifier,
$x_j$ is the relative abundance of $j^{th}$ strain, and
$l'_j$ is effective reference microbial sequence length of strain i.

The relative abundance is computed using the internal unique reference identifier, the external taxonomic identifier, the L2 index, the sequence length and the read length.

In an embodiment, for a total reads from strain $S_i$ is given by $x_i * R$ where R is the plurality of read sequences in the metagenomic sample. The absolute abundance $b_i$ of strain $S_i$ is given by:

$$b_i = \sum_{s_i \in S'} \frac{x_i \cdot R \cdot \hat{r}}{l_i \cdot c}$$

where:
$l_i$ is effective reference microbial sequence length of strain i,
R is the plurality of microbial read sequences in sample,
i is the unique internal identifier, which is associated to an external taxonomic identifier,
$b_i$ s the absolute abundance of strain i,
$\hat{r}$ is the average read length of the reads in a metagenomic sample,
c is the sequencing depth of the metagenomic sample,
$x_i$ is the length adjusted relative abundance of strain i, and
the metric $x_i$. R. $\hat{r}/l_i$ is the measure of sequence coverage of strain i.

Experiment:

Experimented have been conducted to understand the performance of the disclosed technique. The experiment has been conducted with multiple datasets, each containing strains from across the various kingdoms of prokaryotes. For species level profiling, we considered three metagenomic read dataset from two community challenges, namely, the MOSAIC Challenge and the CAMI (Critical Assessment of Metagenome Interpretation) (2nd CAMI Human Microbiome Project Toy dataset from Gastrointestinal tract) Challenge.

The MOSAIC dataset consisted of one high complexity data and one low complexity data each with four different samples. The low complexity dataset consisted of a total of 21 strains spanning 21 species and high complexity dataset consisted of 269 strains from across 90 species. Since universal taxonomic IDs are missing at the strain level, the MOSAIC datasets are for strain level comparisons. The CAMI dataset consisted of three samples, each with 63 strains spanning 38 species. For the strain level profiling, three synthetic datasets were used, namely, LC, which is a low complexity data with consisting of 50 strains from 41 species in total, and HC-1 and HC-2, which are high complexity data consisting of 34 strains from 10 species and 60 strains from 25 species respectively.

The L1 index and L2 index have been constructed using been available sources for biomedical data, including National Center for Biotechnology Information (NCBI), Ensembl, UCSC Genome browser etc, Refseq (complete genomes), Mosaic Challenge that were not present in the Refseq collection. In total MAGE reference database consisted of 24,146 strains from 13,168 species. The species were from 3,559 genus belonging to Virus, Bacteria, Archae, Fungi and Protozoa. The final index for the disclosed technique was â¼ 38 GB in size.

A wide variety of metrics are utilized to compare the profiling outputs with the ground truth. The relative abundance distributions are compared using well-known divergence measures for probability distributions to compare abundance distributions, the Jensen-Shannon divergence, Total variation distance, Hellinger distance and cumulative abundance mass.

The results are simulated for the above test data using the disclosed technique and the performance is documented at strain level and species level.

For three synthetic datasets namely, High complexity (HC)-1, HC-2, and Low complexity (LC) is simulated to generate Illumina paired end reads of 150 bp length and with 20× coverage. Both HC-1 and HC-2 datasets are high complexity metagenomic samples, where multiple strains from same species or species with same genus are present in a sample, such that the constituent strains bear high similarity. The LC dataset is a low complexity data with consisting of 50 strains from 41 species in total and spanning 38 genera. HC-1 and HC-2 are high complexity datasets, where HC-1 consists of 34 strains from 10 species spanning 8 genera and HC-2 consists of 60 strains from 25 species spanning 25 genera. The strain level output of MetaPhlAn2 was mapped to the NCBI taxonomy to compare them with the ground truth. The results in Table 1, Table 2 and Table 3 shows the comparison of disclosed technique with state of art techniques of Centrifuge and MetaPhlAn2 on the high complexity datasets HC-1 and HC-2 and the low complexity data LC. The disclosed technique could detect and estimate abundances of 97% (33 out of 34 strains) of the true strains for the HC-1 dataset, 96% (58 out of 60) of the true strains for the HC-2 dataset, and 100% the of true strains (all the 50 strains) for the LC dataset.

TABLE 1

Strain level profiling performances on HC-1 data

| Tool | MetaPhlAn2 | Centrifuge1 | Centrifuge2 | Disclosed technique |
|---|---|---|---|---|
| JSD (Jensen-Shannon divergence) | 0.0556 | 0.6663 | 0.3813 | 0.9383 |
| TVD (Total Variation distance) | 0.0074 | 0.317 | 0.1619 | 0.9655 |
| Hellinger | 0.1111 | 0.7133 | 0.3824 | 0.9566 |
| Total Mass | 0.0331 | 0.1888 | 0.0012 | 0.8381 |
| Precision Recall Area Under the Curve (PR-AUC) | 0.0556 | 0.6663 | 0.3813 | 0.9383 |
| ROC-AUC (Receiver Operating Characteristic - Area under the Curve) | 0.0074 | 0.317 | 0.1619 | 0.9655 |
| Mean Prec | 0.1111 | 0.7133 | 0.3824 | 0.9566 |

TABLE 2

Strain level profiling performances on HC-2 data

| Tool | MetaPhlAn2 | Centrifuge1 | Centrifuge2 | Disclosed technique |
|---|---|---|---|---|
| JSD (Jensen-Shannon divergence) | 0.6621 | 0.5341 | 0.6843 | 0.0901 |
| TVD (Total Variation distance) | 0.9588 | 0.8061 | 0.9982 | 0.2033 |
| Hellinger | 0.9776 | 0.8783 | 0.9892 | 0.3706 |
| Total Mass | 0.0436 | 0.2167 | 0.0018 | 0.8308 |
| Precision Recall Area Under the Curve (PR-AUC) | 0.0417 | 0.6307 | 0.5817 | 0.9075 |
| ROC-AUC (Receiver Operating Characteristic - Area under the Curve) | 0.0109 | 0.2661 | 0.2839 | 0.9203 |
| Mean Prec | 0.0595 | 0.6611 | 0.5825 | 0.9184 |

TABLE 3

Strain level profiling performances on LC data

| Tool | MetaPhlAn2 | Centrifuge1 | Centrifuge2 | Disclosed technique |
|---|---|---|---|---|
| JSD | 0.6092 | 0.5029 | 0.6897 | 0.0544 |
| TVD | 0.8941 | 0.7732 | 0.9994 | 0.2523 |
| Hellinger | 0.9246 | 0.8452 | 0.9942 | 0.27 |
| Total Mass | 0.2055 | 0.3016 | 0.0006 | 0.9389 |
| PR-AUC | 0.1592 | 0.8149 | 0.5873 | 0.9739 |
| ROC-AUC | 0.049 | 0.3463 | 0.3202 | 0.9942 |
| Mean Prec | 0.1792 | 0.847 | 0.6061 | 0.9907 |

Further for comparing species level profiling results a high complexity and low complexity datasets from MOSAIC Challenge are utilized. The MOSAIC Challenge dataset consisted of HiSeq2500 150 bp paired-end reads with 20× coverage that were simulated using an ART simulator using the StrainMetaSim pipeline. The MOSAIC metagenome samples were segregated as challenge and training dataset. For high complexity data, "sim high" MOSAIC challenge dataset consisting of 269 strains from across 190 species is used. For low complexity data, the "sim low" MOSAIC training dataset consisting of 21 strains across 21 species is used. The results are shown in Table 4 and Table 5. For both high and low complexity dataset, the scores are averaged over four different samples. The low complexity data is particularly challenging because many of the true abundance values were less than 1%. Thus, the disclosed technique could perform well even in such scenarios.

TABLE 4

Comparison of species level profiling performances on high leve complexity MOSAIC challenge data

| Tool | Bracken1 | Bracken2 | MetaPhlAn2 | Centrifuge1 | Centrifuge2 | Disclosed technique |
|---|---|---|---|---|---|---|
| JSD | 0.4847 | 0.4823 | 0.1103 | 0.6404 | 0.6326 | 0.0643 |
| TVD | 0.7341 | 0.7316 | 0.2566 | 0.9616 | 0.9368 | 0.2304 |
| Hellinger | 0.809 | 0.8061 | 0.3875 | 0.9512 | 0.9227 | 0.276 |
| Total Mass | 0.4509 | 0.4586 | 0.8618 | 0.1646 | 0.5709 | 0.951 |
| PR-AUC | 0.867 | 0.8702 | 0.9045 | 0.4382 | 0.3212 | 0.9525 |
| ROC-AUC | 0.5963 | 0.5962 | 0.6394 | 0.2216 | 0.55 | 0.7675 |
| Mean Prec | 0.8715 | 0.8747 | 0.9099 | 0.4426 | 0.3241 | 0.9578 |

TABLE 5

Comparison of species level profiling performances on low level complexity MOSAIC challenge data

| Tool | Bracken1 | Bracken2 | MetaPhlAn2 | Centrifuge1 | Centrifuge2 | Disclosed technique |
|---|---|---|---|---|---|---|
| JSD | 0.134 | 0.1341 | 0.0966 | 0.585 | 0.3525 | 0.0311 |
| TVD | 0.2315 | 0.2315 | 0.2302 | 0.9546 | 0.6169 | 0.1468 |
| Hellinger | 0.3759 | 0.3764 | 0.3159 | 0.9217 | 0.6858 | 0.1943 |
| Total Mass | 0.8794 | 0.8783 | 0.9076 | 0.0454 | 0.4048 | 0.9598 |
| PR-AUC | 0.7701 | 0.7663 | 0.6202 | 0.1383 | 0.263 | 0.8062 |
| ROC-AUC | 0.6639 | 0.6637 | 0.5758 | 0.1221 | 0.7172 | 0.7627 |
| Mean Prec | 0.8065 | 0.8028 | 0.8494 | 0.2282 | 0.2747 | 0.8475 |

Further the species level profiling results have also been benchmarked using the 2nd CAMI Toy Human Microbiome Project dataset, wherein the dataset has simulated metagenome data from five different body sites of human host, namely, gastrointestinal tract, oral cavity, airways, skin, and urogenital tract. The genomes in the samples were taken from the NCBI Refseq complete genomes. The ground truths for all the samples were available along with the metagenomic read samples. The metagenomic samples are paired-end illumina (Hiseq platform) reads with average read-length of 150 bp. Three samples from the gastrointestinal tract have been considered for experimentation and the results in Table 6 are averaged across these three samples.

TABLE 6

Comparison of species level profiling performances on CAMI challenge data

| Tool | Bracken1 | Bracken2 | MetaPhlAn2 | Centrifuge1 | Centrifuge2 | Disclosed technique |
|---|---|---|---|---|---|---|
| JSD | 0.0103 | 0.0123 | 0.1335 | 0.2184 | 0.6269 | 0.0501 |
| TVD | 0.0926 | 0.1041 | 0.2636 | 0.3829 | 0.9482 | 0.2278 |
| Hellinger | 0.1103 | 0.1263 | 0.3769 | 0.5494 | 0.8647 | 0.2724 |
| Total Mass | 0.9909 | 0.9854 | 0.958 | 0.7072 | 0.9972 | 0.9681 |
| PR-AUC | 0.9346 | 0.8943 | 0.9289 | 0.938 | 0.9237 | 0.9274 |
| ROC-AUC | 0.9853 | 0.9849 | 0.6541 | 0.1404 | 0.4166 | 0.841 |
| Mean Prec | 0.9478 | 0.9075 | 0.959 | 0.9978 | 0.9739 | 0.9516 |

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

This disclosure relates generally to a method and a system for profiling of metagenome samples. Most state of-art techniques for metagenomic profiling use homology-based, curated database of identified marker sequences generated after complex and costly pre-processing. The disclosed method and system for profiling of metagenome samples are a non-homology based, a non-marker based and an alignment free strain level profiling tools for microbe profiling. The disclosure works with a several k-mer based indexing techniques for constructing a compact and comprehensive multi-level indexing, wherein the multi-level indexing includes a L1-Index and a L2-Index. The multi-level indexing is used for profiling metagenomics by abundance estimation, wherein the abundance estimation includes a relative abundance and an absolute abundance.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method for profiling of metagenome sample comprising:

receiving a plurality of reference microbial sequences, via one or more hardware processors, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier;

segregating the plurality of reference microbial sequences to obtain a plurality of pre-defined reference chunks using a segregation technique based on the plurality of genus, via the one or more hardware processors, wherein the plurality of pre-defined reference chunks comprises the plurality of strain level sequences belonging to the plurality of genus and the plurality of pre-defined reference chunks is associated with a plurality of indices;

indexing the plurality of pre-defined reference chunks to generate a L1-Index and L2-Index based on an L1-L2 indexing technique, via the one or more hardware processors, wherein the L1-L2 indexing technique comprises:

generating a L2-Index from the plurality of pre-defined reference chunks, wherein generation of the L2-Index comprises:

generating a plurality of L2 k-mers from the plurality of strain level sequences of the plurality of pre-defined reference chunks using on a k-merization technique based on a pre-defined L2 k-value;

indexing each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier;

generating a L1-Index from the plurality of pre-defined reference chunks, wherein generation of the L1-Index comprises:

generating a plurality of L1 k-mers from the plurality of strain level sequences of the plurality of pre-defined reference chunks using on the k-merization technique based on a pre-defined L1 k-value;

indexing the plurality of L1 k-mers to obtain the L1-Index based on a binary encoding technique and a numerical encoding technique, wherein the L1-Index is a map of the L1 k-mers and the indices of the plurality of pre-defined reference chunks;

receiving a plurality of microbial read sequences, via one or more hardware processors, wherein the microbial read sequences is a metagenome sample and each microbial read sequence from the plurality of microbial read sequences is associated with a read length and a sequencing depth; and profiling the plurality of microbial read sequences, via one or more hardware processors, based on the L1-Index and the L2-Index, wherein the profiling the plurality of microbial read sequences at a profile taxonomic hierarchy comprises:

generating a plurality of L1 query k-mers and a plurality of L2 query k-mers for the plurality of microbial read sequences based on a pre-defined L1 k-value and a pre-defined L2 k-value respectively using the k-merization technique;

identifying from the L1-index, a matching reference plurality of pre-defined reference chunks and the corresponding plurality of indices for the plurality of L1 query k-mers;

identifying from the L2-Index, the plurality of strain level sequences and the internal unique reference identifier for the plurality of L2 query k-mers based on the matching reference plurality of pre-defined reference chunks and the plurality of indices; and profiling the plurality of microbial read sequences, wherein the profiling comprises performing an abundance estimation of the plurality of strain level sequences based on an estimation technique using the strain level sequences, the internal unique reference identifier and the sequence length.

2. The processor-implemented method of claim 1, wherein the taxonomic hierarchy comprises one or more of a plurality of phyla, a plurality of classes, a plurality of orders, a plurality of families, a plurality of genera, a plurality of species, a plurality of subspecies and a plurality of strains.

3. The processor-implemented method of claim 1, wherein the k-merization technique includes generation of a plurality of k-mers from the plurality of pre-defined reference chunks, wherein the plurality of pre-defined reference chunks is in form of a string of characters and the generated k-mers are sub-strings of a pre-defined length 'k' from the string of characters.

4. The processor-implemented method of claim 1, wherein the indexing technique comprises one of a FM Indexing technique, a R Indexing technique, a bowtie indexing technique, a suffix tree or suffix array technique, a Rabin-Karp technique, a KMP (Knuth Morris Pratt) technique, a Boyer Moore technique and a De Bruijn Graph.

5. The processor-implemented method of claim 1, wherein the profile taxonomic hierarchy is dynamically selected from the taxonomic hierarchy by a user based on the user's requirement.

6. The processor-implemented method of claim 1, wherein the binary encoding includes conversion of the plurality of pre-defined reference chunks into a binary string and the numerical encoding includes conversion of the binary string to an integer, and wherein the integer indicates a k-mer.

7. The processor-implemented method of claim 1, wherein the estimation technique is a mathematical estimation technique that includes one of a Maximum Likelihood Estimation technique, a Lasso regression technique, a Bayesian Estimation technique.

8. The processor-implemented method of claim 1, the abundance estimation includes a relative abundance and an absolute abundance, wherein the relative abundance is computed using the internal unique reference identifier, the external taxonomic identifier, the L2 index, the sequence length and the read length, and the absolute abundance is computed using the internal unique reference identifier, the external taxonomic identifier, the L2 index, the sequence length, the read length and the sequencing depth of the plurality of microbial read sequences.

9. A system comprising:
a memory storing instructions;
one or more communication interfaces; and
one or more hardware processors coupled to the memory via the one or more communication interfaces, wherein the one or more hardware processors are configured by the instructions to:
receive a plurality of reference microbial sequences, via one or more hardware processors, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier;
segregate the plurality of reference microbial sequences to obtain a plurality of pre-defined reference chunks using a segregation technique based on the plurality of genus, via the one or more hardware processors, wherein the plurality of pre-defined reference chunks comprises the plurality of strain level sequences belonging to the plurality of genus and the plurality of pre-defined reference chunks is associated with a plurality of indices;
index the plurality of pre-defined reference chunks to generate a L1-Index and L2-Index based on an L1-L2 indexing technique, via the one or more hardware processors, wherein the L1-L2 indexing technique comprises:
generate a L2-Index from the plurality of pre-defined reference chunks, wherein generation of the L2-Index comprises:
generate a plurality of L2 k-mers from the plurality of strain level sequences of the plurality of pre-defined reference chunks using on a k-merization technique based on a pre-defined L2 k-value;
index each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier;
generate a L1-Index from the plurality of pre-defined reference chunks, wherein generation of the L1-Index comprises:
generate a plurality of L1 k-mers from the plurality of strain level sequences of the plurality of pre-defined reference chunks using on the k-merization technique based on a pre-defined L1 k-value;
index the plurality of L1 k-mers to obtain the L1-Index based on a binary encoding technique and a numerical encoding technique, wherein the L1-Index is a map of the L1 k-mers and the indices of the plurality of pre-defined reference chunks;
receive a plurality of microbial read sequences, via one or more hardware processors, wherein the microbial read sequences is a metagenome sample and each microbial read sequence from the plurality of microbial read sequences is associated with a read length and a sequencing depth; and profile the plurality of microbial read sequences, via one or more hardware processors, based on the L1-Index and the L2-Index, wherein the profiling the plurality of microbial read sequences at a profile taxonomic hierarchy comprises:
generate a plurality of L1 query k-mers and a plurality of L2 query k-mers for the plurality of microbial read sequences based on a pre-defined L1 k-value and a pre-defined L2 k-value respectively using the k-merization technique;
identify from the L1-index, a matching reference plurality of pre-defined reference chunks and the corresponding plurality of indices for the plurality of L1 query k-mers;
identify from the L2-Index, the plurality of strain level sequences and the internal unique reference identifier for the plurality of L2 query k-mers based on the matching reference plurality of pre-defined reference chunks and the plurality of indices; and
profile the plurality of microbial read sequences, wherein the profiling comprises performing an abundance estimation of the plurality of strain level sequences based on an estimation technique using the strain level sequences, the internal unique reference identifier and the sequence length.

10. The system of claim 9, wherein the one or more hardware processors are configured by the instructions to perform the k-merization technique, wherein the k-merization technique includes generation of a plurality of k-mers from the plurality of pre-defined reference chunks, wherein the plurality of pre-defined reference chunks is in form of a string of characters and the generated k-mers are sub-strings of a pre-defined length 'k' from the string of characters.

11. The system of claim 9, wherein the one or more hardware processors are configured by the instructions to perform the indexing technique, wherein the indexing technique comprises one of a FM Indexing technique, a R Indexing technique, a bowtie indexing technique, a suffix tree or suffix array technique, a Rabin-Karp technique, a KMP (Knuth Morris Pratt) technique, a Boyer Moore technique and a De Bruijn Graph.

12. The system of claim 9, wherein the one or more hardware processors are configured by the instructions to perform the binary encoding and the numerical encoding, wherein the binary encoding includes conversion of the plurality of pre-defined reference chunks into a binary string and the numerical encoding includes conversion of the binary string to an integer, and wherein the integer indicates a k-mer.

13. The system of claim 9, wherein the one or more hardware processors are configured by the instructions to perform the estimation technique, wherein the estimation technique is a mathematical estimation technique that includes one of a Maximum Likelihood Estimation technique, a Lasso regression technique, a Bayesian Estimation technique.

14. The system of claim 9, wherein the one or more hardware processors are configured by the instructions to perform the abundance estimation, wherein the abundance estimation includes a relative abundance and an absolute abundance, wherein the relative abundance is computed using the internal unique reference identifier, the external taxonomic identifier, the L2 index, the sequence length and the read length, and the absolute abundance is computed using the internal unique reference identifier, the external taxonomic identifier, the L2 index, the sequence length, the read length and the sequencing depth of the plurality of microbial read sequences.

15. One or more non-transitory machine readable information storage mediums comprising one or more instructions which when executed by one or more hardware processors cause:
receiving a plurality of reference microbial sequences, wherein the plurality of reference microbial sequences is a collection of a plurality of strain level sequences from across a set of species belonging to a plurality of genus according to a taxonomic hierarchy and each reference microbial sequence from the plurality of reference microbial sequences is associated with a sequence length, an internal unique reference identifier and a corresponding external taxonomic identifier, and wherein the corresponding external taxonomic identifier comprises a strain identifier and a species identifier;
segregating the plurality of reference microbial sequences to obtain a plurality of pre-defined reference chunks using a segregation technique based on the plurality of genus, wherein the plurality of pre-defined reference chunks comprises the plurality of strain level sequences belonging to the plurality of genus and the plurality of pre-defined reference chunks is associated with a plurality of indices;
indexing the plurality of pre-defined reference chunks to generate a L1-Index and L2-Index based on an L1-L2 indexing technique, wherein the L1-L2 indexing technique comprises:
generating a L2-Index from the plurality of pre-defined reference chunks, wherein generation of the L2-Index comprises:
generating a plurality of L2 k-mers from the plurality of strain level sequences of the plurality of pre-defined reference chunks using on a k-merization technique based on a pre-defined L2 k-value;
indexing each L2 k-mer from the plurality of L2 k-mers of each of the pre-defined reference chunks to obtain the L2-Index based on an indexing technique, wherein the L2-index is a strain level sequences mapping of the L2 k-mers, a corresponding location of the L2 k-mers and the internal unique reference identifier;
generating a L1-Index from the plurality of pre-defined reference chunks, wherein generation of the L1-Index comprises:
generating a plurality of L1 k-mers from the plurality of strain level sequences of the plurality of pre-defined reference chunks using on the k-merization technique based on a pre-defined L1 k-value;
indexing the plurality of L1 k-mers to obtain the L1-Index based on a binary encoding technique and a numerical encoding technique, wherein the L1-Index is a map of the L1 k-mers and the indices of the plurality of pre-defined reference chunks;
receiving a plurality of microbial read sequences, wherein the microbial read sequences is a metagenome sample and each microbial read sequence from the plurality of microbial read sequences is associated with a read length and a sequencing depth; and
profiling the plurality of microbial read sequences, based on the L1-Index and the L2-Index, wherein the profiling the plurality of microbial read sequences at a profile taxonomic hierarchy comprises:

generating a plurality of L1 query k-mers and a plurality of L2 query k-mers for the plurality of microbial read sequences based on a pre-defined L1 k-value and a pre-defined L2 k-value respectively using the k-merization technique;

identifying from the L1-index, a matching reference plurality of pre-defined reference chunks and the corresponding plurality of indices for the plurality of L1 query k-mers;

identifying from the L2-Index, the plurality of strain level sequences and the internal unique reference identifier for the plurality of L2 query k-mers based on the matching reference plurality of pre-defined reference chunks and the plurality of indices; and profiling the plurality of microbial read sequences, wherein the profiling comprises performing an abundance estimation of the plurality of strain level sequences based on an estimation technique using the strain level sequences, the internal unique reference identifier and the sequence length.

* * * * *